United States Patent
Fujimaki et al.

(10) Patent No.: US 8,722,723 B2
(45) Date of Patent: May 13, 2014

(54) AROMATIC AMIDE DERIVATIVE

(75) Inventors: Nobuko Fujimaki, Tokyo (JP); Madoka Nakagomi, Kanagawa (JP); Koichi Shudo, Tokyo (JP)

(73) Assignee: Research Foundation Itsuu Laboratory, Tokyo (JP)

( * ) Notice: Subject to any disclaimer, the term of this patent is extended or adjusted under 35 U.S.C. 154(b) by 314 days.

(21) Appl. No.: 12/919,267

(22) PCT Filed: Feb. 27, 2009

(86) PCT No.: PCT/JP2009/053640
§ 371 (c)(1),
(2), (4) Date: Nov. 30, 2010

(87) PCT Pub. No.: WO2009/107762
PCT Pub. Date: Sep. 3, 2009

(65) Prior Publication Data
US 2011/0071304 A1    Mar. 24, 2011

(30) Foreign Application Priority Data
Feb. 28, 2008   (JP) .................................. 2008-047078

(51) Int. Cl.
*A61K 31/4015* (2006.01)
*C07D 209/36* (2006.01)

(52) U.S. Cl.
USPC ........................... 514/416; 548/472; 548/486

(58) Field of Classification Search
USPC ....................................................... 548/472
See application file for complete search history.

(56) References Cited

U.S. PATENT DOCUMENTS

| | | |
|---|---|---|
| 2,841,591 A | 7/1958 | Prichard |
| 5,650,386 A | 7/1997 | Leone-Bay et al. |
| 6,090,958 A | 7/2000 | Leone-Bay et al. |

FOREIGN PATENT DOCUMENTS

| | | |
|---|---|---|
| JP | 2002-506418 | 2/2002 |
| WO | 2007/109211 | 9/2007 |

OTHER PUBLICATIONS

Heemskerk, et al. Document No. 147:385820, retrieved from CAPLUS; Sep. 28, 2007.*
Suizu, et al. Document No. 140:138723, retrieved from CAPLUS; Sep. 23, 2003.*
Jacob, et al. Document No. 139:6753, retrieved from CAPLUS; Apr. 7, 2003.*
Ebel, et al. Document No. 52:113795, retrieved from CAPLUS; Apr. 22, 2001.*
Jieping Wan et al., "Novel one-step synthesis of 2-carbonyl/thiocarbonyl isoindolinones and mechanistic disclosure on the rearrangement reaction of o-phthalaldehyde with amide/thioamide analogs", Tetrahedron, pp. 9338-9344, (2007).
Mamiko Suizu et al., "Cyclooxygenese Inhibitors Derived from Thalidomide", Chem. Pharm. Bull., Jul. 2003, pp. 1098-1102.
Andrea Leone-Bay et al., "4- [4- [(2-Hydroxybenzoyl) amino] phenyl] butryric Acid as a Novel Oral Delivery Agent for Recombinant Human Growth Hormone", Journal of Medicinal Chemistry pp. 2571-2578, (1996).
Ronald Grigg et al., "Isoindolinones via a room temperature palladium nanoparticle-catalysed 3-component cyclative carbonylation-amination cascade", Tetrahedron Letters, Jul. 2003, pp. 6979-6982.
Shunsuke Murahashi et al., "Studies on the High Pressure Reaction of Carbon Monoxide. II. Synthesis of Phthalimidine", Bull. Chem. Soc. Japan, pp. 81-88, (1960).
Delacroix et al., "Preparation of Functionalized Arylmagnesium Reagents Bearing an o-Chloromethyl Group", J. Org. Chem., 65, pp. 8108-8110, 2000.
International Search Report and International Search Report and/or Preliminary Report on Patentability, dated May 12, 2009.
English Translation of International Search Report and International Search Report and/or Preliminary Report on Patentability, dated May 12, 2009.
Japanese Office Action, mail date is Aug. 20, 2013, with partial English translation thereof.

* cited by examiner

*Primary Examiner* — Shawquia Young
(74) *Attorney, Agent, or Firm* — Greenblum & Bernstein, P.L.C.

(57) ABSTRACT

A compound represented by the following general formula (I) ($R^1$ and $R^2$ represent hydrogen atom, an alkyl group, a halogen atom, etc.; $R^3$ and $R^4$ represent hydrogen atom, an alkyl group, an alkoxy group, or an alkenyl group; $R^5$ represents hydrogen atom, an alkyl group, or nitro group, and $R^6$ represents hydrogen atom or an alkyl group), which acts on the transcription process of genes.

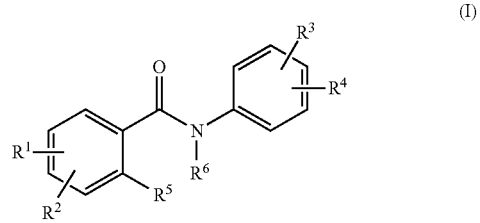

(I)

7 Claims, No Drawings

AROMATIC AMIDE DERIVATIVE

TECHNICAL FIELD

The present invention relates to an aromatic amide derivative which acts on the transcription process of genes.

BACKGROUND ART

Transcription is a synthesis process of messenger RNA (mRNA) by an RNA polymerase using a nucleotide sequence of genomic DNA as a template, which is the first stage for gene expression. In a broad sense, transcription means synthesis of a certain nucleic acid by using another nucleic acid as a template, and for example, synthesis of mRNA from an RNA genome of an RNA virus may also be called transcription. Transcription comprises processes of initiation, extension, and termination, and by the time of the initiation, various transcription factors are involved in activation and suppression of transcription. A compound which directly or indirectly acts on this transcription process has a physiological activity, such as regulation of gene expression, and usefulness thereof is expected as a medicament or agricultural chemical.

As aromatic amide derivatives, the compounds disclosed in Non-patent documents 1 to 4 and the like are known. However, physiological activities of these compounds on the transcription process are not known. Although an aromatic amide compound having a COX inhibitory action is known (Non-patent document 5), transcription inhibition action is not known also for this compound.

Non-patent document 1: Bull. Chem. Soc. Japan, 33, pp. 81-88, 1960
Non-patent document 2: Tetrahedron Letters, 44, pp. 6979-6982, 2003
Non-patent document 3: Tetrahedron, 63, 9338, 200
Non-patent document 4: J. Org. Chem., 65, pp. 8108-8110, 2000
Non-patent document 5: Chem. Pharm. Bull., 51, pp. 1098-1102, 2003

DISCLOSURE OF THE INVENTION

Object to be Achieved by the Invention

An object of the present invention is to provide a compound which acts on the transcription process of genes.

Means for Achieving the Object

As a method for choosing substances which act on the transcription process of genes, the reporter assay is used, in which expression of a protein encoded by a specific gene (reporter gene) is measured A method in which activity of a luciferase is measured as the reporter protein has been widely used. In the course of screening for compounds specifically inhibiting or promoting the enzymatic activity of firefly luciferase (Luc) for aiming at providing compounds having a transcription regulation action, the inventors of the present invention found that compounds represented by following general formula (I) had extremely strong desired action.

The present invention thus provides a compound represented by the following general formula (I):

[Formula 1]

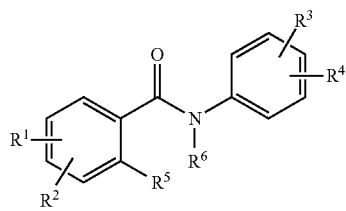

(I)

(wherein $R^1$ and $R^2$ independently represent a group selected from the group consisting of hydrogen atom, an alkyl group, a halogen atom, amino group, a mono- or dialkyl-substituted amino group, nitro group, an alkoxy group, and carboxylic acid; $R^3$ and $R^4$ independently represent a group selected from the group consisting of hydrogen atom, an alkyl group, an alkoxy group, and an alkenyl group (the alkyl group, alkoxy group and alkenyl group may be substituted with one carboxyl group, and the carboxyl group may form an ester); $R^5$ represents hydrogen atom, an alkyl group, or nitro group, $R^6$ represents hydrogen atom or an alkyl group, and $R^5$ and $R^6$ may bind together to become methylene group ($-CH_2-$) or ethylene group ($-CH_2CH_2-$) and thereby form a 5- or 6-membered ring; provided that when $R^1$ and $R^2$ both are hydrogen atoms, $R^3$ is not hydrogen atom, and $R^5$ and $R^6$ bind together to represent methylene group; when $R^3$ and $R^4$ both are hydrogen atoms, $R^1$ is not hydrogen atom, and $R^5$ and $R^6$ bind together to represent methylene group; and when $R^3$ and $R^4$ both are alkyl groups, $R^5$ and $R^6$ bind together to represent methylene group), or a salt thereof.

According to a preferred embodiment of the aforementioned invention, there is provided the aforementioned compound or a salt thereof, wherein $R^5$ and $R^6$ bind together to represent methylene group. As embodiments of this preferred embodiment, there are provided the aforementioned compound or a salt thereof, wherein $R^1$ is hydrogen atom, a halogen atom, amino group, a mono- or dialkyl-substituted amino group, or nitro group, and $R^2$ is hydrogen atom; and the aforementioned compound or a salt thereof, wherein $R^3$ is hydrogen atom, an alkyl group, an alkoxy group, or an alkenyl group (the alkyl group, alkoxy group and alkenyl group may be substituted with one carboxyl group, and the carboxyl group may form an ester), and $R^4$ is hydrogen atom.

According to another preferred embodiment of the aforementioned invention, there is provided the aforementioned compound or a salt thereof, wherein $R^5$ is hydrogen atom, an alkyl group, or nitro group, and $R^6$ is hydrogen atom, and as embodiments of this preferred embodiments, there are provided the aforementioned compound or a salt thereof, wherein $R^1$ is an alkyl group, amino group, a mono- or dialkyl-substituted amino group, or nitro group, and $R^2$ is hydrogen atom; and the aforementioned compound or a salt thereof, wherein $R^3$ is an alkyl group (the alkyl group may be substituted with one carboxyl group, and the carboxyl group may form an ester), and $R^4$ is hydrogen atom.

As a further preferred embodiment, there is provided the aforementioned compound or a salt thereof, wherein $R^5$ and $R^6$ bind together to represent methylene group, $R^1$ is a halogen atom, amino group, or a mono- or dialkyl-substituted amino group, $R^2$ is hydrogen atom, $R^3$ is an alkyl group (the alkyl group may be substituted with one carboxyl group or one alkoxycarbonyl group), and $R^4$ is hydrogen atom. As a particularly preferred embodiment, there is provided the aforementioned compound or a salt thereof, wherein $R^5$ and $R^6$ bind together to represent methylene group, $R^1$ is a halogen atom (for example, fluorine atom), or a dialkyl-substituted amino group (for example, dimethylamino group), $R^2$ is hydrogen atom, $R^3$ is an alkyl group (the alkyl group may be substituted with one carboxyl group or one alkoxycarbonyl group), and $R^4$ is hydrogen atom.

As other aspects, the present invention provides an agent for regulating luciferase activity, which comprises a compound represented by the aforementioned general formula (I) or a salt thereof, an agent for regulating luminescence of a bioluminescence system containing a luciferase and luciferin, which comprises a compound represented by the aforementioned general formula (I) or a salt thereof, a method for regulating luciferase activity, which comprises the step of contacting a compound represented by the aforementioned general formula (I) or a salt thereof with a luciferase, and a method for regulating luminescence of a bioluminescence system containing a luciferase and luciferin, which comprises the step of adding a compound represented by the aforementioned general formula (I) or a salt thereof to the system.

Effect of the Invention

The compound or a salt thereof of the present invention has an action of specifically inhibiting or promoting the enzymatic activity of firefly luciferase, thus usefulness thereof as a compound acting on the transcription process of genes is expected, and the compound can also be used as an agent for regulating bioluminescence.

BEST MODE FOR CARRYING OUT THE INVENTION

In this specification, the alkyl group may be a linear, branched, or cyclic alkyl group, or an alkyl group consisting of a combination thereof. Although the carbon number of the alkyl group is not particularly limited, the carbon number is preferably about 1 to 10, more preferably about 1 to 8, particularly preferably about 1 to 6. The same shall apply to an alkyl moiety of other substituents having an alkyl moiety (alkoxy group and the like). The alkenyl group may be a linear, branched, or cyclic alkenyl group, or an alkenyl group consisting of a combination thereof. Although the carbon number of the alkenyl group is not particularly limited, the carbon number is preferably about 2 to 10, more preferably about 2 to 6, particularly preferably about 2 to 4. Although the number of double bond contained in the alkenyl group is not particularly limited, the number is, for example, 1 or 2, preferably 1. As the halogen atom, any of fluorine atom, chlorine atom, bromine atom and iodine atom may be used.

$R^1$ and $R^2$ may exist at an arbitrary substitutable position on the benzene ring. As the alkyl group represented by $R^1$ or $R^2$, for example, a linear or branched alkyl group having about 1 to 6 carbon atoms is preferred. As the halogen atom represented by $R^1$ or $R^2$, fluorine atom is preferred. As the mono- or dialkyl-substituted amino group represented by $R^1$ or $R^2$, for example, methylamino group, dimethylamino group, ethylamino group, ethylmethylamino group, diethylamino group, propylamino group; butylamino group, pentylamino group, hexylamino group, heptylamino group, and the like can be exemplified, but the group is not limited to these examples. As the alkoxy group represented by $R^1$ or $R^2$, for example, a linear or branched alkoxy group having about 1 to 6 carbon atoms is preferred, and methoxy group, ethoxy group and the like can be more preferably used.

$R^3$ and $R^4$ may exist at an arbitrary substitutable position on the benzene ring. As the alkyl group represented by $R^3$ or $R^4$, a linear, branched, or cyclic alkyl group having about 1 to 10 carbon atoms, or an alkyl group consisting of a combination thereof is preferred, and a linear, branched, or cyclic alkyl group having about 1 to 8 carbon atoms can be more preferably used. When the alkyl group is not substituted with carboxyl group or an ester thereof, the alkyl group is preferably a linear, branched or cyclic alkyl group having about 3 to 8 carbon atoms. When the alkyl group is substituted with carboxyl group or an ester thereof, it is preferably a linear or branched alkyl group having about 2 to 6 carbon atoms.

As the alkoxy group represented by $R^3$ or $R^4$, a linear or branched alkoxy group having about 1 to 8 carbon atoms is preferred, and a linear or branched alkoxy group having about 1 to 6 carbon atoms can be more preferably used. The alkoxy group is preferably substituted with carboxyl group or an ester thereof, and in this case, as the alkoxy group, a linear or branched alkoxy group having about 1 to 4 carbon atoms is preferred. As the alkenyl group represented by $R^3$ or $R^4$, a linear, branched or cyclic alkenyl group having about 2 to 8 carbon atoms, or an alkenyl group consisting of a combination thereof is preferred, and a linear or branched alkenyl group having about 2 to 6 carbon atoms can be more preferably used. The alkenyl group is preferably substituted with carboxyl group or an ester thereof, and in this case, as the alkenyl group, a linear or branched alkenyl group having about 2 to 4 carbon atoms is preferred.

The alkyl group, alkoxy group and alkenyl group represented by $R^3$ or $R^4$ may have one carboxyl group at an arbitrary position. The residue which forms the ester is not particularly limited, and examples of preferred groups for ester residue include, for example, methyl group, ethyl group, propyl group, isopropyl group, butyl group, isobutyl group, t-butyl group, benzyl group, acetoxymethyl group, 1-(acetoxy) ethyl group, propionyloxymethyl group, 1-(propionyloxy) ethyl group, butyryloxymethyl group, 1-(butyryloxy)ethyl group, isobutyryloxymethyl group, 1-(isobutyryloxy)ethyl group, valeryloxymethyl group, 1-(valeryloxy)ethyl group, isovaleryloxymethyl group, 1-(isovaleryloxy)ethyl group, pivaloyloxymethyl group, 1-(pivaloyloxy)ethyl group, methoxycarbonyloxymethyl group, 1-(methoxycarbonyloxy) ethyl group, ethoxycarbonyloxymethyl group, 1-(ethoxycarbonyloxy)ethyl group, propoxycarbonyloxymethyl group, 1-(propoxycarbonyloxy)ethyl group, isopropoxycarbonyloxymethyl group, 1-(isopropoxycarbonyloxy)ethyl group, butoxycarbonyloxymethyl group, 1-(butoxycarbonyloxy) ethyl group, isobutoxycarbonyloxymethyl group, 1-(isobutoxycarbonyloxy)ethyl group, t-butoxycarbonyloxymethyl group, 1-(t-butoxycarbonyloxy)ethyl group, cyclopentanecarbonyloxymethyl group, 1-(cyclopentanecarbonyloxy) ethyl group, cyclohexanecarbonyloxymethyl group, 1-(cyclohexanecarbonyloxy)ethyl group, cyclopentyloxycarbonyloxymethyl group, 1-(cyclopentyloxycarbonyloxy)ethyl group, cyclohexyloxycarbonyloxymethyl group, 1-(cyclohexyloxycarbonyloxy)ethyl group, benzoyloxymethyl group, 1-(benzoyloxy)ethyl group, phenoxycarbonyloxymethyl group, 1-(phenoxycarbonyloxy)ethyl group, (5-methyl-2-oxo-1,3-dioxolen-4-yl)methyl group, 2-trimethylsilylethyl group, and the like. Among these groups for ester residues, alkyl groups such as methyl group and ethyl group are preferred, and as the ester, alkyl esters are preferred.

As the alkyl group represented by $R^5$ or $R^6$, for example, a linear or branched alkyl group having about 1 to 6 carbon atoms is preferred, methyl group or ethyl group is more preferred, and methyl group is particularly preferred. $R^5$ and $R^6$ may bind together to become methylene group ($-CH_2-$) or ethylene group ($-CH_2CH_2-$) and thereby form a 5- or 6-membered ring together with the carbon atom and the nitrogen atom to which they bind.

The compounds where $R^5$ and $R^6$ bind together to become methylene group and thereby form a 5-membered ring constitute a particularly preferred embodiment of the compound of the present invention. In this preferred embodiment, it is preferred that $R^1$ is hydrogen atom, a halogen atom, amino group, a mono- or dialkyl-substituted amino group or nitro group, and $R^2$ is hydrogen atom. In this preferred embodiment, it is preferred that $R^3$ is hydrogen atom, an alkyl group, an alkoxy group, or an alkenyl group (the alkyl group, alkoxy group or alkenyl group may be substituted with one carboxyl group, and the carboxyl group may form an ester), and $R^4$ is hydrogen atom.

In this preferred embodiment, it is preferred that $R^1$ is a halogen atom, amino group, or a mono- or dialkyl-substituted amino group, $R^2$ is a hydrogen atom, $R^3$ is an alkyl group (the alkyl group may be substituted with one carboxyl group or one alkoxycarbonyl group), and $R^4$ is hydrogen atom, and it is more preferred that $R^1$ is a halogen atom (for example, fluorine atom), or a dialkyl-substituted amino group (for example, dimethylamino group), $R^2$ is hydrogen atom, $R^3$ is an alkyl group (the alkyl group is, for example, a linear or branched alkyl group having 1 to 4 carbon atoms, and may be substituted with one carboxyl group or one alkoxycarbonyl group), and $R^4$ is hydrogen atom. It is particularly preferred that $R^1$ is fluorine atom or dimethylamino group, $R^2$ is hydrogen atom, and $R^3$ is propyl group substituted with one carboxyl group or one alkoxycarbonyl group. The alkoxy group constituting the alkoxycarbonyl group is preferably, for example, an alkoxy group having 1 to 4 carbon atoms, and examples include, for example, methoxy group, ethoxy group, n-propoxy group, isopropoxy group, n-butoxy group, sec-butoxy group, tert-butoxy group, and the like. When $R^2$ is hydrogen atom, it is preferred that $R^1$ exists at the meta-position (the meta position not adjacent to the amide group is preferred) or the para-position of $R^5$, and it is particularly preferred that $R^1$ exists at the para-position of $R^5$.

Further, in this preferred embodiment, it is preferred that $R^1$ is amino group or a mono- or dialkyl-substituted amino group, $R^2$ is hydrogen atom, $R^3$ is an alkyl group or an alkoxy group, and $R^4$ is hydrogen atom, and it is more preferred that $R^1$ is a dialkyl-substituted amino group (for example, dimethylamino group), $R^2$ is hydrogen atom, $R^3$ is an alkyl group or an alkoxy group, and $R^4$ is hydrogen atom. It is particularly preferred that $R^1$ is dimethylamino group, $R^2$ is hydrogen atom, $R^3$ is a linear or branched alkyl group having 3 to 5 carbon atoms or a cyclic alkyl group having 5 to 7 carbon atoms, or $R^3$ is an alkoxy group having 1 to 4 carbon atoms, and $R^4$ is hydrogen atom. When $R^2$ is hydrogen atom, it is preferred that $R^1$ exists at the meta-position (the meta position not adjacent to the amide group is preferred) or the para-position of $R^5$.

As another embodiment, it is also preferred that $R^5$ is hydrogen atom, an alkyl group or nitro group, and $R^6$ is hydrogen atom. In this preferred embodiment, it is preferred that $R^1$ is an alkyl group, amino group, a mono-or dialkyl-substituted amino group or nitro group, and $R^2$ is hydrogen atom. Further, in this preferred embodiment, it is also preferred that $R^3$ is an alkyl group (the alkyl group may be substituted with one carboxyl group, and the carboxyl group may form an ester), and $R^4$ is hydrogen atom.

In the compounds represented by the aforementioned general formula (I), when both $R^1$ and $R^2$ are hydrogen atoms, $R^3$ is not hydrogen atom, and $R^5$ and $R^6$ bind together to represent methylene group. In this case, $R^3$ is preferably an alkyl group, more preferably an alkyl group substituted with carboxyl group or an ester thereof. Further, when both $R^3$ and $R^4$ are hydrogen atoms, $R^1$ is not hydrogen atom, and $R^5$ and $R^6$ bind together to represent methylene group. In this case, it is preferred that $R^1$ is amino group, or a monoalkyl or dialkyl-substituted amino group, and it is more preferred that $R^1$ is a dialkylamino group.

The compounds of the present invention may have one or two or more asymmetric carbon atoms depending on types of substituents. Any optical isomers based on these asymmetric carbon atoms, any mixtures of optical isomers, racemates, diastereomers based on two or more asymmetric carbon atoms, any mixtures of diastereomers and the like fall within the scope of the present invention. Further, any hydrates or solvates of the compounds in free form or in the form of a salt also fall within the scope of the present invention.

The compounds of the present invention represented by the general formula (I) may exist in the form of a salt such as an acid addition salt or a base addition salt, and any of such salts falls within the scope of the present invention. Examples of the acid addition salt include mineral acid salts such as hydrochloride and hydrobromide, and organic acid salts such as p-toluenesulfonate, methanesulfonate, oxalate and tartrate. As the base addition salt, for example, metal salts such as sodium salt, potassium salt, magnesium salt and calcium salt, ammonium salts, organic amine salts such as triethylamine salt and ethanolamine salt, and the like can be used. The compounds may also exist as an amino acid salt such as glycine salt, or an alkyl group can further be introduced into the dialkylamino group to form a quaternary salt.

In the examples contained in this specification, the methods for preparing the aforementioned preferred compounds falling within the scope of the aforementioned general formula (I) are specifically explained. Therefore, by appropriately choosing starting materials, reaction reagents, reaction conditions and the like used in these preparation methods, and adding appropriate modification or alteration to these preparation methods as required, any of the compounds falling within the scope of the present invention can be prepared. However, the preparation method of the compounds of the present invention is not limited to the methods specifically explained in the examples.

The compounds and salts thereof of the present invention have an action of inhibiting the enzyme activity of firefly luciferase as specifically shown in the examples mentioned below, and usefulness thereof is expected as a compound which acts on the transcription process of genes. A luminescence system of firefly luciferin/luciferase is used as, for example, an inspection system for contamination with microorganisms such as bacteria, and because the compounds and salts thereof of the present invention have an action of specifically promoting or inhibiting the firefly luciferin/luciferase, they can be used as an agent for regulating luminescence for a luminescence system using the firefly luciferin/luciferase.

EXAMPLES

The present invention will be more specifically explained with reference to examples. However, the scope of the present invention is not limited to the range of the following examples. The compounds prepared in the examples are mentioned below. In the table, Me represents methyl group, Et represents ethyl group, nPro represents n-propyl group, iPro represents isopropyl group, nBu represents n-butyl group, tBu represents tert-butyl group, and Cyclohexyl represents cyclohexyl group. In the table, for example, "3-NMe$_2$" mentioned in the column of "$R^1R^2$" means that dimethylamino group as $R^1$ binds at the 3-position of the benzene ring on the left side in the following formula (I), and $R^2$ is hydrogen atom in this case. Further, for example, "3-(CH$_2$)$_3$CO$_2$H" mentioned in the column of "R$^3$R$^4$" means that a group of —(CH$_2$)$_3$CO$_2$H as R$^3$ binds at the 3-position of the benzene ring on the right side in the following formula (I), and R$^4$ is hydrogen atom in this case. CH$_2$ mentioned in the column of "R$^5$R$^6$" means that R$^5$ and R$^6$ bind together to become methylene group, and in this case, a 5-membered ring is formed with the carbon atom and the nitrogen atom to which they bind.

TABLE 1

(I)

| Ex. | R$^1$ R$^2$ | R$^3$ R$^4$ | R$^5$ | R$^6$ |
|---|---|---|---|---|
| 1 | 3-NMe$_2$ | 3-nPro | CH$_2$ | |
| 2 | 2-NMe$_2$ | 3-nPro | CH$_2$ | |
| 3 | 3-NMe$_2$ | 3-nBu | CH$_2$ | |
| 4 | 2-NMe$_2$ | 3-nBu | CH$_2$ | |
| 5 | 3-NMe$_2$ | 3-iPro | CH$_2$ | |
| 6 | 2-NMe$_2$ | 3-iPro | CH$_2$ | |
| 7 | 3-NMe$_2$ | 3-(CH$_2$)$_6$CH$_3$ | CH$_2$ | |
| 8 | 2-NMe$_2$ | 3-(CH$_2$)$_6$CH$_3$ | CH$_2$ | |
| 9 | 3-NMe$_2$ | 3-(CH$_2$)$_7$CH$_3$ | CH$_2$ | |
| 10 | 2-NMe$_2$ | 3-(CH$_2$)$_7$CH$_3$ | CH$_2$ | |
| 11 | 3-NMe$_2$ | Cyclohexyl | CH$_2$ | |
| 12 | 2-NMe$_2$ | Cyclohexyl | CH$_2$ | |
| 13 | 1-NMe$_2$ | H$_2$ | CH$_2$ | |
| 14 | 2-NMe$_2$ | 3-OMe | CH2 | |
| 15 | 3-NMe$_2$ | 3-(CH$_2$)$_3$CO$_2$Et | CH$_2$ | |
| 16 | 3-NMe$_2$ | 3-(CH$_2$)$_3$CO$_2$H | CH$_2$ | |
| 17 | 2-NMe$_2$ | 3-(CH$_2$)$_3$CO$_2$Et | CH$_2$ | |
| 18 | 2-NMe$_2$ | 3-(CH$_2$)$_3$CO$_2$H | CH$_2$ | |
| 19 | H | 3-(CH$_2$)$_3$CO$_2$Et | CH$_2$ | |
| 20 | H | 3-(CH$_2$)$_3$CO$_2$H | CH$_2$ | |
| 21 | 2-NMe$_2$ | 3-(CH$_2$)$_2$CO$_2$Me | CH$_2$ | |
| 22 | 2-NMe$_2$ | 3-(CH$_2$)$_2$CO$_2$H | CH$_2$ | |
| 23 | H | 3-CH=CHCO$_2$Et | CH$_2$ | |
| 24 | H | 3-CH=CHCO$_2$H | CH$_2$ | |
| 25 | 2-NO$_2$ | 3-OCH$_2$CO$_2$Me | CH2 | |
| 26 | 2-NH$_2$ | 3-OCH$_2$CO$_2$Me | CH2 | |
| 27 | 2-NMe$_2$ | 3-OCH$_2$CO$_2$Me | CH2 | |
| 28 | 2-NMe$_2$ | 3-OCH$_2$CO$_2$H | CH2 | |
| 29 | 2-F | 3-(CH$_2$)$_3$CO$_2$H | CH$_2$ | |
| 30 | 2-NMe$_2$ | 3-(CH$_2$)$_3$CONMe$_2$ | CH$_2$ | |
| 31 | 2-NMe$_2$ | 3-(CH$_2$)$_3$CO$_2$tBu | CH$_2$ | |
| 32 | 2-NMe$_3$I | 3-(CH$_2$)$_3$CO$_2$H | CH$_2$ | |
| 33 | 4-NH(CH$_2$)$_6$CH$_3$ | 2,4-Me$_2$ | CH$_2$ | |
| 34 | 2-NMe$_2$ | 3-(CH$_2$)$_3$CO$_2$H | H | H |
| 35 | 2-NMe$_2$ | 3-(CH$_2$)$_3$CO$_2$Et | Me | H |
| 36 | 2-NMe$_2$ | 3-(CH$_2$)$_3$CO$_2$H | Me | H |
| 37 | 2-NO$_2$ | 3-(CH$_2$)$_3$CO$_2$Et | Me | H |
| 38 | 2-NO$_2$ | 3-(CH$_2$)$_3$CO$_2$H | Me | H |
| 39 | 2-Me | 3-(CH$_2$)$_3$CO$_2$Et | NO$_2$ | H |
| 40 | 2-Me | 3-(CH$_2$)$_3$CO$_2$H | NO$_2$ | H |

Example 1

A solution of 95% 4-nitrophthalic acid anhydride (4.22 g, 20.7 mmol) and 4-propylaniline (2.81 g, 20.7 mmol) in acetic acid (86 ml) was refluxed by heating for 24 hours. The reaction solution was cooled to room temperature, and then added to ice water, and the deposited crystals were collected by filtration, and washed with water. The resulting crystals were purified by recrystallization (ethanol) to obtain 5-nitro-2-(4-propyl-phenyl)-isoindole-1,3-dione as pale yellow scaly crystals (5.89 g, yield: 91.4%).

Example 2

A solution of 5-nitro-2-(4-propyl-phenyl)-isoindole-1,3-dione (3.11 g, 10.03 mmol) obtained in Example 1 and tin (16.66 g, 140.39 mmol) in ethanol (125 ml) was added with concentrated hydrochloric acid (74 ml), and the mixture was stirred with heating at 75° C. for 8 hours. The reaction solution was cooled to room temperature, and then added to 2 N aqueous sodium hydroxide (220 ml), and the mixture was filtered through Cerite. The filtrate was added with chloroform for extraction. The chloroform layer was washed with saturated brine, dried over sodium sulfate, filtered, and concentrated under reduced pressure. The resulting residue was purified by silica gel column chromatography (chloroform: ethyl acetate=30:1) and recrystallization (ethanol) to obtain the objective compounds, 5-amino-2-(4-propyl-phenyl)-isoindol-1-one as a pale yellow powdery substance (1.13 g, yield: 42.3%) and 6-amino-2-(4-propyl-phenyl)-isoindol-1-one as a pale yellow powdery substance (0.27 g, yield: 10.2%).

Example 3

A solution of 5-amino-2-(4-propyl-phenyl)-isoindol-1-one (89 mg, 0.33 mmol) obtained in Example 2 and formalin (0.26 ml) in THF (5 ml) was added with 95% sodium cyanoborohydride (66 mg, 1.00 mmol) and acetic acid (0.1 ml), the mixture was stirred at room temperature for 30 minutes, and then further added with acetic acid (0.1 ml), and the mixture was stirred at room temperature for 7 hours. The reaction solution was added with ethyl acetate for extraction. The ethyl acetate layer was washed with 1 N aqueous potassium hydroxide and saturated brine, dried over sodium sulfate, filtered, and concentrated under reduced pressure. The resulting residue was purified by silica gel column chromatography (chloroform) and recrystallization (chloroform/n-hexane) to obtain 5-dimethylamino-2-(4-propyl-phenyl)-isoindol-1-one (Compound 1) as a pale yellow powdery substance (75.8 mg, yield: 77.1%).

Melting point: 160-161° C.
MS m/z: 265 (100), 294 (M$^+$, 57)
$^1$H-NMR (CDCl$_3$) δ: 0.95 (3H, t, J=7.2 Hz), 1.65 (2H, q, J=7.2 Hz), 2.58 (2H, t, J=7.2 Hz), 3.08 (6H, s), 4.75 (2H, s), 6.70 (1H, s), 6.78 (1H, dd, J=8.4, 2.4 Hz), 7.21 (2H, d, J=8.7 Hz), 7.73 (1H, d, J=8.4 Hz, 7.74 (2H, d, J=8.7 Hz)

Example 4

By using 6-amino-2-(4-propyl-phenyl)-isoindol-1-one obtained in Example 2 instead of 5-amino-2-(4-propyl-phenyl)-isoindol-1-one used in Example 3, synthesis was performed in the same manner as that of Example 3 to obtain 6-dimethylamino-2-(4-propyl-phenyl)-isoindol-1-one (Compound 2) as a pale yellow powdery substance.

Melting point: 141-142° C.
MS m/z: 265 (100), 294 (M$^+$, 93)
$^1$H-NMR (CDCl$_3$) δ: 0.95 (3H, t, J=7.5 Hz), 1.65 (2H, q, J=7.5 Hz), 2.59 (2H, t, J=7.5 Hz), 3.03 (6H, s), 4.75 (2H, s), 6.97 (1H, dd, J=8.4, 2.4 Hz), 7.21 (1H, d, J=2.4 Hz), 7.23 (2H, d, J=8.7 Hz), 7.34 (1H, d, J=8.4 Hz), 7.76 (2H, d, J=8.7 Hz)

Example 5

By using 4-n-butylaniline instead of 4-propylaniline used in Example 1, synthesis was performed in the same manner as that of Example 1 to obtain 5-nitro-2-(4-n-butyl-phenyl)-isoindole-1,3-dione.

Example 6

By using 5-nitro-2-(4-n-butyl-phenyl)-isoindole-1,3-dione obtained in Example 5 instead of 5-nitro-2-(4-propyl-phenyl)-isoindole-1,3-dione used in Example 2, synthesis was performed in the same manner as that of Example 2 to obtain 5-amino-2-(4-n-butyl-phenyl)-isoindol-1-one and 6-amino-2-(4-n-butyl-phenyl)-isoindol-1-one.

Example 7

By using 5-amino-2-(4-n-butyl-phenyl)-isoindol-1-one obtained in Example 6 instead of 5-amino-2-(4-propyl-phenyl)-isoindol-1-one used in Example 3, synthesis was performed in the same manner as that of Example 3 to obtain 5-dimethylamino-2-(4-n-butyl-phenyl)-isoindol-1-one (Compound 3) as a white powdery substance.
Melting point: 133-134° C.
MS m/z: 265 (100), 308 (M+, 54)
$^1$H-NMR (CDCl$_3$) δ: 0.95 (3H, t, J=7.5 Hz), 1.33-1.42 (2H, m), 1.60-1.66 (2H, m), 2.60 (2H, t, J=7.5 Hz), 3.08 (6H, s), 4.75 (2H, s), 6.69 (1H, s), 6.78 (1H, dd, J=8.4, 2.1 Hz), 7.21 (2H, d, J=9.0 Hz), 7.73 (1H, d, J=8.4 Hz), 7.74 (2H, d, J=9.0 Hz)

Example 8

By using 6-amino-2-(4-n-butyl-phenyl)-isoindol-1-one obtained in Example 6 instead of 5-amino-2-(4-propyl-phenyl)-isoindol-1-one used in Example 3, synthesis was performed in the same manner as that of Example 3 to obtain 6-diethylamino-2-(4-n-butyl-phenyl)-isoindol-1-one (Compound 4) as a white powdery substance.
Melting point: 117-118° C.
MS m/z: 265 (100), 308 (M+, 78)
IR (KBr) cm$^{-1}$: 3425, 1684, 1622, 1509, 1446, 1377, 1206, 1050
$^1$H-NMR (CDCl$_3$) δ: 0.93 (3H, t, J=7.5 Hz), 1.28-1.45 (2H, m), 1.56-1.66 (2H, m), 2.61 (2H, t, J=7.5 Hz), 3.03 (6H, s), 4.75 (2H, s), 6.97 (1H, dd, J=8.4, 2.4 Hz), 7.21 (1H, d, J=2.4 Hz), 7.24 (2H, d, J=8.7 Hz), 7.31 (1H, d, J=8.4 Hz), 7.75 (2H, d, J=8.7 Hz)

Example 9

By using 4-isopropylaniline instead of 4-propylaniline used in Example 1, synthesis was performed in the same manner as that of Example 1 to obtain 5-nitro-2-(4-isopropyl-phenyl)-isoindole-1,3-dione.

Example 10

By using 5-nitro-2-(4-isopropyl-phenyl)-isoindole-1,3-dione obtained in Example 9 instead of 5-nitro-2-(4-propyl-phenyl)-isoindole-1,3-dione used in Example 2, synthesis was performed in the same manner as that of Example 2 to obtain 5-amino-2-(4-isopropyl-phenyl)-isoindol-1-one and 6-amino-2-(4-isopropyl-phenyl)-isoindol-1-one.

Example 11

By using 5-amino-2-(4-isopropyl-phenyl)-isoindol-1-one obtained in Example 10 instead of 5-amino-2-(4-propyl-phenyl)-isoindol-1-one used in Example 3, synthesis was performed in the same manner as that of Example 3 to obtain 5-dimethylamino-2-(4-isopropyl-phenyl)-isoindol-1-one (Compound 5) as a pale yellow powdery substance.
Melting point: 167-169° C.
MS m/z: 279 (100), 294 (M+, 62)
$^1$H-NMR (CDCl$_3$) δ: 1.25 (3H, s), 1.27 (3H, s), 2.83-2.96 (1H, mz), 3.07 (6H, s), 4.74 (2H, s), 6.69 (1H, s), 6.78 (1H, dd, J=8.4, 2.4 Hz), 7.26 (2H, d, J=8.4 Hz), 7.74 (1H, d, J=8.41 Hz), 7.75 (2H, d, J=8.4 Hz)

Example 12

By using 6-amino-2-(4-isopropyl-phenyl)-isoindol-1-one obtained in Example 10 instead of 5-amino-2-(4-propyl-phenyl)-isoindol-1-one used in Example 3, synthesis was performed in the same manner as that of Example 3 to obtain 6-dimethylamino-2-(4-isopropyl-phenyl)-isoindol-1-one (Compound 6) as a white powdery substance.
Melting point: 169-170° C.
MS m/z: 279 (100), 294 (M+, 89)
$^1$H-NMR (CDCl$_3$) δ: 1.26 (3H, s), 1.28 (3H, s), 2.83-2.92 (1H, m), 3.03 (6H, s), 4.75 (2H, s), 6.96 (1H, dd, J=8.1, 2.4 Hz), 7.21 (1H, d, J=2.4 Hz), 7.28 (2H, d, J=8.7 Hz), 7.75 (1H, d, J=8.1 Hz), 7.77 (2H, d, J=8.7 Hz)

Example 13

By using 4-heptylaniline instead of 4-propylaniline used in Example 1, synthesis was performed in the same manner as that of Example 1 to obtain 5-nitro-2-(4-n-heptyl-phenyl)-isoindole-1,3-dione.

Example 14

By using 5-nitro-2-(4-n-heptyl-phenyl)-isoindole-1,3-dione obtained in Example 13 instead of 5-nitro-2-(4-propyl-phenyl)-isoindole-1,3-dione used in Example 2, synthesis was performed in the same manner as that of Example 2 to obtain 5-amino-2-(4-n-heptyl-phenyl)-isoindol-1-one and 6-amino-2-(4-n-heptyl-phenyl)-isoindol-1-one.

Example 15

By using 5-amino-2-(4-n-heptyl-phenyl)-isoindol-1-one obtained in Example 14 instead of 5-amino-2-(4-propyl-phenyl)-isoindol-1-one used in Example 3, synthesis was performed in the same manner as that of Example 3 to obtain 5-dimethylamino-2-(4-n-heptyl-phenyl)-isoindol-1-one (Compound 7) as white crystals.
Melting point: 133-134° C.
MS m/z: 265 (100), 350 (M+, 67)
$^{11}$H-NMR (CDCl$_3$) δ: 0.88 (3H, t, J=7.2 Hz), 1.21-1.42 (8H, m), 1.53-1.59 (2H, m), 2.59 (2H, t, J=7.5 Hz), 3.08 (6H, s), 4.75 (2H, s), 6.69 (1H, s), 6.78 (1H, dd, J=8.4, 2.1 Hz), 7.21 (2H, d, J=8.4 Hz), 7.71-7.77 (3H, m)

Example 16

By using 6-amino-2-(4-n-heptyl-phenyl)-isoindol-1-one obtained in Example 14 instead of 5-amino-2-(4-propyl-phenyl)-isoindol-1-one used in Example 3, synthesis was performed in the same manner as that of Example 3 to obtain 6-dimethylamino-2-(4-n-heptyl-phenyl)-isoindol-1-one (Compound 8) as white crystals.
Melting point: 101-102° C.
MS m/z: 265 (100), 350 (M+, 94)
$^1$H-NMR (CDCl$_3$) δ: 0.88 (3H, t, J=7.8 Hz), 1.18-1.42 (8H, m), 1.56-1.61 (2H, m), 2.60 (2H, t, J=7.8 Hz), 3.03 (6H, s), 4.75 (2H, s), 6.96 (1H, dd, J=8.4, 2.4 Hz), 7.16-7.24 (3H, m), 7.34 (1H, d, J=8.4 Hz), 7.75 (2H, d, J=8.4 Hz)

Example 17

By using 4-heptylaniline instead of 4-propylaniline used in Example 1, synthesis was performed in the same manner as that of Example 1 to obtain 5-nitro-2-(4-n-octyl-phenyl)-isoindole-1,3-dione.

Example 18

By using 5-nitro-2-(4-n-octyl-phenyl)-isoindole-1,3-dione obtained in Example 17 instead of 5-nitro-2-(4-propyl-phenyl)-isoindole-1,3-dione used in Example 2, synthesis was performed in the same manner as that of Example 2 to obtain 5-amino-2-(4-n-octyl-phenyl)-isoindol-1-one and 6-amino-2-(4-n-octyl-phenyl)-isoindol-1-one.

Example 19

By using 5-amino-2-(4-n-octyl-phenyl)-isoindol-1-one obtained in Example 18 instead of 5-amino-2-(4-propyl-phenyl)-isoindol-1-one used in Example 3, synthesis was performed in the same manner as that of Example 3 to obtain 5-dimethylamino-2-(4-n-octyl-phenyl)-isoindol-1-one (Compound 9) as a white powdery substance.

Melting point: 128-129° C.
MS m/z: 265 (100), 364 (M$^+$, 96)
$^1$H-NMR (CDCl$_3$) δ: 0.88 (3H, t, J=8.1 Hz), 1.14-1.41 (10H, m), 1.59 (2H, t, J=8.11 Hz), 2.61 (2H, t, J=8.1 Hz), 3.08 (6H, s), 4.75 (2H, s), 6.70 (1H, s), 6.76-6.81 (1H, m), 7.21 (2H, d, J=8.4 Hz), 7.69-7.79 (3H, m)

Example 20

By using 6-amino-2-(4-n-octyl-phenyl)-isoindol-1-one obtained in Example 18 instead of 5-amino-2-(4-propyl-phenyl)-isoindol-1-one used in Example 3, synthesis was performed in the same manner as that of Example 3 to obtain 6-dimethylamino-2-(4-n-octyl-phenyl)-isoindol-1-one (Compound 10) as a white powdery substance.

Melting point: 100-101° C.
MS m/z: 364 (M$^+$, 100)
$^1$H-NMR (CDCl$_3$) δ: 0.88 (3H, t, J=7.2 Hz), 1.12-1.44 (10H, m), 1.62 (2H, t, J=7.2 Hz), 2.60 (2H, t, J=7.2 Hz), 3.03 (6H, s), 4.75 (2H, s), 6.93-6.99 (1H, m), 7.23 (2H, d, J=8.4 Hz), 7.25-7.28 (1H, m), 7.34 (1H, d, J=8.4 Hz), 7.76 (2H, d, J=8.4 Hz)

Example 21

By using 4-heptylaniline instead of 4-propylaniline used in Example 1, synthesis was performed in the same manner as that of Example 1 to obtain 5-nitro-2-(4-cyclohexyl-phenyl)-isoindole-1,3-dione.

Example 22

By using 5-nitro-2-(4-cyclohexyl-phenyl)-isoindole-1,3-dione obtained in Example 21 instead of 5-nitro-2-(4-propyl-phenyl)-isoindole-1,3-dione used in Example 2, synthesis was performed in the same manner as that of Example 2 to obtain 5-amino-2-(4-cyclohexyl-phenyl)-isoindol-1-one and 6-amino-2-(4-cyclohexyl-phenyl)-isoindol-1-one.

Example 23

By using 5-amino-2-(4-cyclohexyl-phenyl)-isoindol-1-one obtained in Example 22 instead of 5-amino-2-(4-propyl-phenyl)-isoindol-1-one used in Example 3, synthesis was performed in the same manner as that of Example 3 to obtain 5-dimethylamino-2-(4-cyclohexyl-phenyl)-isoindol-1-one (Compound 11) as white scaly crystals.

Melting point: 150-151° C.
MS m/z: 176 (100), 258 (M$^+$, 42)
$^1$H-NMR (CDCl$_3$) δ: 1.38-1.85 (10H, m), 3.03 (6H, s), 4.15-4.31 (1H, m), 4.26 (2H, s), 6.67 (1H, s), 6.75 (1H, dd, J=8.7, 2.1 Hz), 7.68 (1H, d, J=8.7 Hz)

Example 24

By using 6-amino-2-(4-cyclohexyl-phenyl)-isoindol-1-one obtained in Example 22 instead of 5-amino-2-(4-propyl-phenyl)-isoindol-1-one used in Example 3, synthesis was performed in the same manner as that of Example 3 to obtain 6-dimethylamino-2-(4-cyclohexyl-phenyl)-isoindol-1-one (Compound 12) as pale orange acicular crystals.

Melting point: 156-157° C.
MS m/z: 176 (100), 258 (M$^+$, 75)
$^1$H-NMR (CDCl$_3$) δ: 1.42-1.93 (10H, m), 3.00 (6H, s), 4.17-4.33 (1H, m), 4.25 (2H, s), 6.90 (1H, dd, J=8.7, 2.4 Hz), 7.17 (1H, d, J=2.4 Hz), 7.28 (1H, d, J=8.7 Hz)

Example 25

A solution of 2-bromomethyl-6-nitro-benzoic acid methyl ester (0.40 g, 1.46 mmol) and aniline (0.23 g, 2.44 mmol) in ethanol (20 ml) was added with pyridine (0.15 g, 1.95 mmol), and the mixture was refluxed by heating for 30 hours. The reaction solution was cooled to room temperature, and then poured into ice water, and the deposited crystals were collected by filtration, washed with ethanol and water, and dried. The resulting crystals were recrystallized (acetone) to obtain 7-nitro-2-phenyl-2,3-dihydro-isoindol-1-one as pale yellow crystals (0.23 g, yield: 62.9%).

Example 26

7-Nitro-2-phenyl-2,3-dihydro-isoindol-1-one (0.19 g) obtained in Example 25 was catalytically reduced in the presence of 10% palladium/carbon (0.18 mg) in benzene (250 ml). The reaction solution was filtered, and concentrated under reduced pressure. The resulting residue was purified by recrystallization (ethanol) to obtain 7-amino-2-phenyl-2,3-dihydro-isoindol-1-one as a pale yellow powdery substance (0.16 g, yield: 96.4%).

Example 27

By using 7-amino-2-phenyl-2,3-dihydroisoindol-1-one obtained in Example 26 instead of 5-amino-2-(4-propyl-phenyl)-isoindol-1-one used in Example 3, synthesis was performed in the same manner as that of Example 3 to obtain 7-dimethylamino-2-phenyl-2,3-dihydro-isoindol-1-one (Compound 13) as a yellow powdery substance.

Melting point: 58-60° C.
MS m/z: 237 (100), 252 (M$^+$, 41)
$^1$H-NMR, (CDCl$_3$) δ: 3.04 (6H, s), 4.78 (2H, s), 6.90 (1H, d, J=8.4 Hz), 6.96 (1H, d, J=8.4 Hz), 7.15 (1H, t, J=8.4 Hz), 7.34-7.47 (3H, m), 7.86 (2H, d, J=8.4 Hz)

Example 28

By using 2-bromomethyl-5-nitrobenzoic acid methyl ester and 4-methoxyaniline instead of 2-bromomethyl-6-nitro-benzoic acid methyl ester and aniline used in Example 25, synthesis was performed in the same manner as that of Example 25 to obtain 6-nitro-2-(4-methoxyphenyl)-2,3-dihydro-isoindol-1-one.

Example 29

By using 6-nitro-2-(4-methoxyphenyl)-2,3-dihydro-isoindol-1-one obtained in Example 28 instead of 6-nitro-2-(4-methoxyphenyl)-2,3-dihydro-isoindol-1-one used in Example 26, synthesis was performed in the same manner as that of Example 26 to obtain 6-amino-2-(4-methoxyphenyl)-2,3-dihydro-isoindol-1-one.

Example 30

By using 6-amino-2-(4-methoxyphenyl)-2,3-dihydro-isoindol-1-one obtained in Example 29 instead of 5-amino-2-(4-propyl-phenyl)-isoindol-1-one used in Example 3, synthesis was performed in the same manner as that of Example 3 to obtain 7-dimethylamino-2-(4-methoxyphenyl)-2,3-dihydro-isoindol-1-one (Compound 14) as a pale yellow powdery substance.
Melting point: 145-146° C.
MS m/z: 282 (M$^+$, 100)
$^1$H-NMR (CDCl$_3$) δ: 3.03 (6H, s), 3.83 (3H, s), 4.74 (2H, s), 6.96 (2H, d, J=9.6 Hz), 6.96-6.98 (1H, m), 7.18-7.38 (2H, m), 7.75 (2H, d, J=9.6 Hz)

Example 31

By using 2-bromomethyl-4-nitrobenzoic acid methyl ester and 4-(4-aminophenyl)butyric acid ethyl ester instead of 2-bromomethyl-6-nitro-benzoic acid methyl ester and aniline used in Example 25, synthesis was performed in the same manner as that of Example 25 to obtain 4-[4-(5-nitro-1-oxo-1,3-dihydro-isoindol-2-yl)-phenyl]-butyric acid ethyl ester.

Example 32

By using 4-[4-(5-nitro-1-oxo-1,3-dihydro-isoindol-2-yl)-phenyl]-butyric acid ethyl ester obtained in Example 31 instead of 6-nitro-2-(4-methoxyphenyl)-2,3-dihydro-isoindol-1-one used in Example 26, synthesis was performed in the same manner as that of Example 26 to obtain 4-[4-(5-amino-1-oxo-1,3-dihydro-isoindol-2-yl)-phenyl]-butyric acid ethyl ester.

Example 33

By using 4-[4-(5-amino-1-oxo-1,3-dihydro-isoindol-2-yl)-phenyl]-butyric acid ethyl ester obtained in Example 32 instead of 5-amino-2-(4-propyl-phenyl)-isoindol-1-one used in Example 3, synthesis was performed in the same manner as that of Example 3 to obtain 4-[4-(5-dimethylamino-1-oxo-1,3-dihydro-isoindol-2-yl)-phenyl]-butyric acid ethyl ester (Compound 15) as a white powdery substance.
Melting point: 116-117° C.
MS m/z: 265 (100), 366 (M$^+$, 63)
$^1$H-NMR (CDCl$_3$) δ: 1.26 (3H, t, J=7.5 Hz), 1.96 (2H, t, J=7.5 Hz), 2.33 (2H, t, J=7.5 Hz), 2.65 (2H, t, J=7.8 Hz), 3.08 (6H, s), 4.13 (2H, q, J=7.8 Hz), 4.74 (2H, s), 6.69 (1H, d, J=2.1 Hz), 6.78 (1H, dd, J=8.4, 2.1 Hz), 7.15-7.28 (2H, m), 7.69-7.83 (3H, m)

Example 34

A solution of 4-[4-(5-dimethylamino-1-oxo-1,3-dihydro-isoindol-2-yl)-phenyl]-butyric acid ethyl ester (0.13 g, 0.35 mmol) obtained in Example 33 in ethanol (15 ml) was added with 0.5 M NaOH aq. (3.3 ml), and the mixture was stirred at room temperature for 10 hours. The reaction solution was made acidic by adding 10% hydrochloric acid, and then extracted with chloroform. The chloroform layer was washed with saturated brine, dried over sodium sulfate, filtered, and concentrated under reduced pressure. The resulting residue was purified by silica gel column chromatography (chloroform:methanol=20:1) and recrystallization (ethanol) to obtain 4-[4-(5-dimethylamino-1-oxo-1,3-dihydro-isoindol-2-yl)-phenyl]-butyric acid (Compound 16) as a pale brown powdery substance (79.4 mg, yield: 66.7%).
Melting point: 179-180° C.
MS m/z: 265 (100), 338 (M$^+$, 67)
$^1$H-NMR (CDCl$_3$) δ: 1.98 (2H, t, J=7.5 Hz), 2.39 (2H, t, J=7.5 Hz), 2.68 (2H, t, J=7.8 Hz), 3.08 (6H, s), 4.74 (2H, s), 6.70 (1H, d, J=2.1 Hz), 6.78 (1H, dd, J=8.4, 2.1 Hz), 7.18-7.28 (2H, m), 7.69-7.81 (3H, m)

Example 35

By using 2-bromomethyl-5-nitrobenzoic acid methyl ester and 4-(4-amino-phenyl)butyric acid ethyl ester instead of 2-bromomethyl-6-nitro-benzoic acid methyl ester and aniline used in Example 25, synthesis was performed in the same manner as that of Example 25 to obtain 4-[4-(6-nitro-1-oxo-1,3-dihydro-isoindol-2-yl)-phenyl]-butyric acid ethyl ester.

Example 36

By using 4-[4-(6-nitro-1-oxo-1,3-dihydro-isoindol-2-yl)-phenyl]-butyric acid ethyl ester obtained in Example 35 instead of 6-nitro-2-(4-methoxyphenyl)-2,3-dihydro-isoindol-1-one used in Example 26, synthesis was performed in the same manner as that of Example 26 to obtain 4-[4-(6-amino-1-oxo-1,3-dihydro-isoindol-2-yl)-phenyl]-butyric acid ethyl ester.

Example 37

By using 4-[4-(6-amino-1-oxo-1,3-dihydro-isoindol-2-yl)-phenyl]-butyric acid ethyl ester obtained in Example 36 instead of 5-amino-2-(4-propyl-phenyl)-isoindol-1-one used in Example 3, synthesis was performed in the same manner as that of Example 3 to obtain 4-[4-(6-dimethylamino-1-oxo-1,3-dihydro-isoindol-2-yl)-phenyl]-butyric acid ethyl ester (Compound 17) as a white powdery substance.
Melting point: 86-87° C.
MS m/z: 388 (M$^+$, 100)
$^1$H-NMR (CDCl$_3$) δ: 1.26 (3H, t, J=7.2 Hz), 1.96 (2H, quin, J=7.5 Hz), 2.33 (2H, t, J=7.5 Hz), 2.66 (2H, t, J=7.5 Hz), 3.03 (6H, s), 4.13 (2H, q, J=7.5 Hz), 4.75 (2H, s), 6.96 (1H, dd, J=8.4, 2.4 Hz), 7.21 (1H, d, J=2.4 Hz), 7.23 (2H, d, J=8.4 Hz), 7.34 (1H, d, J=8.4 Hz), 7.77 (2H, d, J=8.4 Hz)

Example 38

By using 4-[4-(6-dimethylamino-1-oxo-1,3-dihydro-isoindol-2-yl)-phenyl]-butyric acid ethyl ester obtained in Example 37 instead of 4-[4-(5-dimethylamino-1-oxo-1,3-dihydro-isoindol-2-yl)-phenyl]-butyric acid ethyl ester used in Example 34, synthesis was performed in the same manner as that of Example 34 to obtain 4-[4-(6-dimethylamino-1-oxo-1,3-dihydro-isoindol-2-yl)-phenyl]-butyric acid (Compound 18) as a pale brown powdery substance.
Melting point: 186-187° C.
MS m/z: 55 (100), 338 (M$^+$, 96)

$^1$H-NMR (CDCl$_3$) δ: 1.99 (2H, quin, J=7.5 Hz), 2.39 (2H, t, J=7.5 Hz), 2.69 (2H, t, J=7.5 Hz), 3.03 (6H, s), 4.75 (2H, s), 6.97 (1H, dd, J=8.4, 2.4 Hz), 7.21 (1H, d, J=2.4 Hz), 7.24 (2H, d, J=8.4 Hz), 7.34 (1H, d, J=8.4 Hz), 7.77 (2H, d, J=8.4 Hz)

Example 39

By using 2-bromomethyl-benzoic acid methyl ester and 4-(4-amino-phenyl)butyric acid ethyl ester instead of 2-bromomethyl-6-nitro-benzoic acid methyl ester and aniline used in Example 25, synthesis was performed in the same manner as that of Example 25 to obtain 4-[4-(1-oxo-1,3-dihydro-isoindol-2-yl)-phenyl]-butyric acid ethyl ester (Compound 19) as a white powdery substance.

Melting point: 94-96° C.

MS m/z: 57 (100), 323 (M$^+$, 24)

$^1$H-NMR (CDCl$_3$) δ: 1.26 (3H, t, J=7.2 Hz), 1.97 (2H, t, J=7.5 Hz), 2.33 (2H, t, J=7.5 Hz), 2.67 (2H, t, J=7.5 Hz), 4.14 (2H, q, J=7.2 Hz), 4.85 (2H, s), 7.50-7.60 (4H, m), 7.70-7.83 (3H, m), 7.91-7.95 (1H, m)

Example 40

By using 4-[4-(1-oxo-1,3-dihydro-isoindol-2-yl)-phenyl]-butyric acid ethyl ester obtained in Example 39 instead of 4-[4-(5-dimethylamino-1-oxo-1,3-dihydro-isoindol-2-yl)-phenyl]-butyric acid ethyl ester used in Example 34, synthesis was performed in the same manner as that of Example 34 to obtain 4-[4-(1-oxo-1,3-dihydro-isoindol-2-yl)-phenyl]-butyric acid (Compound 20) as a brown powdery substance.

Melting point: 128-129° C.

MS m/z: 57 (100), 222 (65), 295 (M$^+$, 28)

$^1$H-NMR (CDCl$_3$) δ: 1.99 (2H, t, J=7.5 Hz), 2.40 (2H, t, J=7.5 Hz), 2.70 (2H, t, J=7.5 Hz), 4.86 (2H, s), 7.25 (2H, d, J=8.7 Hz), 7.45-7.62 (3H, m), 7.77 (2H, d, J=8.7 Hz), 7.91-7.95 (1H, m)

Example 41

By using 2-bromomethyl-5-nitrobenzoic acid ethyl ester and 3-(4-amino-phenyl)propionic acid methyl ester instead of 2-bromomethyl-6-nitro-benzoic acid methyl ester and aniline in Example 25, synthesis was performed in the same manner as that of Example 25 to obtain 3-[4-(6-nitro-1-oxo-1,3-dihydro-isoindol-2-yl)-phenyl]-propionic acid methyl ester as yellow crystals.

Example 42

By using 3-[4-(6-nitro-1-oxo-1,3-dihydro-isoindol-2-yl)-phenyl]-propionic acid methyl ester obtained in Example 41 instead of 6-nitro-2-(4-methoxyphenyl)-2,3-dihydro-isoindol-1-one used in Example 26, synthesis was performed in the same manner as that of Example 26 to obtain 3-[4-(6-amino-1-oxo-1,3-dihydro-isoindol-2-yl)-phenyl]-propionic acid methyl ester as an orange oily substance.

Example 43

By using 3-[4-(6-amino-1-oxo-1,3-dihydro-isoindol-2-yl)-phenyl]-propionic acid methyl ester obtained in Example 42 instead of 5-amino-2-(4-propyl-phenyl)-isoindol-1-one used in Example 3, synthesis was performed in the same manner as that of Example 3 to obtain 3-[4-(6-dimethylamino-1-oxo-1,3-dihydro-isoindol-2-yl)-phenyl]-propionic acid methyl ester (Compound 21) as yellow crystals.

Melting point: 123-124° C.

MS m/z: 251 (100), 265 (95), 324 (65), 338 (M$^+$, 81)

$^1$H-NMR (CDCl$_3$) δ: 2.64 (2H, t, J=7.8 Hz), 2.96 (2H, t, J=7.8 Hz), 3.03 (6H, s), 3.68 (3H, s), 4.75 (2H, s), 6.96 (1H, dd, J=8.1, 2.4 Hz), 7.20 (1H, d, J=2.1 Hz), 7.24 (2H, d, J=9.0 Hz), 7.34 (1H, d, J=8.1 Hz), 7.78 (2H, d, J=9.0 Hz)

Example 44

By using 3-[4-(6-dimethylamino-1-oxo-1,3-dihydro-isoindol-2-yl)-phenyl]-propionic acid methyl ester obtained in Example 43 instead of 4-[4-(5-dimethylamino-1-oxo-1,3-dihydro-isoindol-2-yl)-phenyl]-butyric acid ethyl ester used in Example 34, synthesis was performed in the same manner as that of Example 34 to obtain 3-[4-(6-dimethylamino-1-oxo-1,3-dihydro-isoindol-2-yl)-phenyl]-propionic acid (Compound 22) as a white powdery substance.

Melting point: 200-201° C.

MS m/z: 265 (100), 324 (M$^+$, 94)

$^1$H-NMR (CDCl$_3$) δ: 2.70 (2H, t, J=7.8 Hz), 2.96 (2H, t, J=7.8 Hz), 3.03 (6H, s), 4.75 (2H, s), 6.97 (1H, dd, J=8.4, 2.4 Hz), 7.21 (1H, d, J=2.4 Hz), 7.27 (2H, d, J=8.4 Hz), 7.34 (1H, d, J=8.4 Hz), 7.79 (2H, d, J=8.4 Hz)

Example 45

By using 2-bromomethyl-benzoic acid ethyl ester and 4-aminocinnamic acid ethyl ester instead of 2-bromomethyl-6-nitro-benzoic acid methyl ester and aniline used in Example 25, synthesis was performed in the same manner as that of Example 25 to obtain 3-[4-(1-oxo-1,3-dihydro-isoindol-2-yl)-phenyl]-acrylic acid ethyl ester (Compound 23) as white crystals.

Melting point: 184-185° C.

MS m/z: 307 (M$^+$, 100)

$^1$H-NMR (CDCl$_3$) δ: 1.35 (3H, t, J=7.5 Hz), 4.27 (2H, q, J=7.5 Hz), 4.89 (2H, s), 6.42 (1H, d, J=15.9 Hz), 7.52-7.63 (5H, m), 7.68 (1H, d, J=15.9 Hz), 7.91-7.98 (3H, m)

Example 46

By using 3-[4-(1-oxo-1,3-dihydro-isoindol-2-yl)-phenyl]-acrylic acid ethyl ester obtained in Example 45 instead of 4-[4-(5-dimethylamino-1-oxo-1,3-dihydro-isoindol-2-yl)-phenyl]-butyric acid ethyl ester used in Example 34, synthesis was performed in the same manner as that of Example 34 to obtain 3-[4-(1-oxo-1,3-dihydro-isoindol-2-yl)-phenyl]-acrylic acid (Compound 24) as a brown powdery substance.

Melting point: higher than 300° C.

MS m/z: 279 (M$^+$, 100)

$^1$H-NMR (CDCl$_3$) δ: 4.92 (2H, s), 6.41 (1H, d, J=15.9 Hz), 7.51-7.64 (5H, m), 7.69 (1H, d, J=15.9 Hz), 7.92-7.95 (3H, m)

Example 47

By using 2-bromomethyl-5-nitrobenzoic acid ethyl ester and (4-amino-phenoxy)-acetic acid methyl ester instead of 2-bromomethyl-6-nitro-benzoic acid methyl ester and aniline used in Example 25, synthesis was performed in the same manner as that of Example 25 to obtain [4-(6-nitro-1-oxo-1,3-dihydro-isoindol-2-yl)-phenoxy]-acetic acid methyl ester (Compound 25) as a yellow green powdery substance.

Melting point: 238-239° C.

MS m/z: 269 (100), 342 (M$^+$, 75)

¹H-NMR (CDCl₃) δ: 3.83 (3H, s), 4.71 (2H, s), 4.95 (2H, s), 7.01 (2H, d, J=9.0 Hz), 7.70 (1H, d, J=8.1 Hz), 7.75 (2H, d, J=9.0 Hz), 8.49 (1H, dd, J=8.1, 2.4 Hz), 8.76 (1H, d, J=2.4 Hz)

Example 48

By using [4-(6-nitro-1-oxo-1,3-dihydro-isoindol-2-yl)-phenoxy]-acetic acid methyl ester obtained in Example 47 instead of 6-nitro-2-(4-methoxyphenyl)-2,3-dihydro-isoindol-1-one used in Example 26, synthesis was performed in the same manner as that of Example 26 to obtain [4-(6-amino-1-oxo-1,3-dihydro-isoindol-2-yl)-phenoxy]-acetic acid methyl ester (Compound 26) as a pale yellow powdery substance.

Melting point: 197-198° C.
MS m/z: 239 (100), 312 (M⁺, 75)
¹H-NMR, (CDCl₃) δ: 3.79 (3H, s), 4.60 (2H, brs), 4.74 (2H, s), 4.84 (2H, s), 6.97-7.07 (3H, m), 7.08-7.12 (1H, m), 7.32 (1H, d, J=8.4 Hz), 6.96 (2H, d, J=9.0 Hz), 7.18 (1H, d, J=2.1 Hz), 7.27 (1H, d, J=7.8 Hz), 7.73 (2H, d, J=9.0 Hz)

Example 49

By using [4-(6-amino-1-oxo-1,3-dihydro-isoindol-2-yl)-phenoxy]-acetic acid methyl ester obtained in Example 48 instead of 5-amino-2-(4-propyl-phenyl)-isoindol-1-one used in Example 3, synthesis was performed in the same manner as that of Example 3 to obtain [4-(6-dimethylamino-1-oxo-1,3-dihydro-isoindol-2-yl)-phenoxy]-acetic acid methyl ester (Compound 27) as a pale yellow powdery substance.

Melting point: 167-168° C.
MS m/z: 57 (100), 267 (20), 340 (M⁺, 22)
¹H-NMR (CDCl₃) δ: 3.03 (6H, s), 3.82 (3H, s), 4.66 (2H, s), 4.73 (2H, s), 6.93-7.03 (3H, m), 7.21 (1H, d, J=2.4 Hz), 7.34 (1H, d, J=8.4 Hz), 7.77 (2H, d, J=9.0 Hz)

Example 50

By using [4-(6-dimethylamino-1-oxo-1,3-dihydro-isoindol-2-yl)-phenoxy]-acetic acid methyl ester obtained in Example 49 instead of 4-[4-(5-dimethylamino-1-oxo-1,3-dihydro-isoindol-2-yl)-phenyl]-butyric acid ethyl ester used in Example 34, synthesis was performed in the same manner as that of Example 34 to obtain [4-(6-dimethylamino-1-oxo-1,3-dihydro-isoindol-2-yl)-phenoxy]-acetic acid (Compound 28) as a pale brown powdery substance.

Melting point: 206-208° C.
MS m/z: 43 (100), 267 (80), 326 (M⁺, 77)
¹H-NMR (CD₃OD) δ: 3.01 (6H, s), 4.20 (2H, s), 4.63 (2H, s), 6.98-7.13 (3H, s), 7.40-7.44 (1H, m), 7.57-7.81 (3H, m)

Example 51

By using 2-bromomethyl-5-fluorobenzoic acid ethyl ester and 4-(4-amino-phenyl)butyric acid ethyl ester instead of 2-bromomethyl-6-nitro-benzoic acid methyl ester and aniline used in Example 25, synthesis was performed in the same manner as that of Example 25 to obtain 4-[4-(6-fluoro-1-oxo-1,3-dihydro-isoindol-2-yl)-phenyl]-butyric acid ethyl ester as an orange oily substance.

Example 52

By using 4-[4-(6-fluoro-1-oxo-1,3-dihydro-isoindol-2-yl)-phenyl]-butyric acid ethyl ester obtained in Example 51 instead of 4-[4-(5-dimethylamino-1-oxo-1,3-dihydro-isoindol-2-yl)-phenyl]-butyric acid ethyl ester used in Example 34, synthesis was performed in the same manner as that of Example 34 to obtain 4-[4-(6-fluoro-1-oxo-1,3-dihydro-isoindol-2-yl)-phenyl]-butyric acid (Compound 29) as a brown powdery substance.

Melting point: 172-173° C.
MS m/z: 240 (100), 313 (M⁺, 42)
¹H-NMR (CDCl₃) δ: 1.92 (3H, t, J=7.2 Hz), 2.31 (2H, t, J=7.5 Hz), 2.68 (2H, t, J=7.5 Hz), 3.01 (2H, s), 7.26-7.32 (2H, m), 7.40-7.71 (3H, m), 7.73-7.77 (2H, m)

Example 53

A solution of 4-[4-(6-dimethylamino-1-oxo-1,3-dihydro-isoindol-2-yl)-phenyl]-butyric acid (85 mg, 0.25 mM) obtained in Example 38 in THF (3 ml) was added dropwise with triethylamine (0.20 g, 2.00 mM), and 2,4,6-trichlorobenzoyl chloride (0.31 g, 1.25 mM) under ice cooling, and the mixture was stirred at room temperature for 3 hours. The reaction solution was added dropwise with a 2 M solution of dimethylamine in THF (0.63 ml) and triethylamine (0.20 g, 2.00 mM) under ice cooling, and added with dimethylaminopyridine (46 mg, 0.38 mM), and the mixture was stirred at room temperature for 4 hours. The reaction solution was added with ammonium chloride and ethyl acetate for extraction. The ethyl acetate layer was washed with saturated brine, dried, and concentrated under reduced pressure. The resulting residue was purified by silica gel column chromatography (chloroform:methanol=20:1) and recrystallization (ethanol) to obtain 4-[4-(6-dimethylamino-1-oxo-1,3-dihydro-isoindol-2-yl)-phenyl]-N,N-dimethyl-butylamide (Compound 30) as a pale yellow powdery substance (85 mg, yield: 93.0%).

Melting point: 148-149° C.
MS m/z: 279 (100), 365 (M⁺, 33)
¹H-NMR (CDCl₃) δ: 1.99 (2H, t, J=7.5 Hz), 2.33 (2H, t, J=7.5 Hz), 2.69 (2H, t, J=7.5 Hz), 2.95 (6H, s), 3.03 (6H, s), 4.76 (2H, s), 6.96 (1H, dd, J=8.4, 2.4 Hz), 7.20 (1H, d, J=2.4 Hz), 7.25 (1H, d, J=8.4 Hz), 7.34 (1H, d, J=8.4 Hz), 7.77 (2H, d, J=8.4 Hz)

Example 54

A solution of 4-[4-(6-dimethylamino-1-oxo-1,3-dihydro-isoindol-2-yl)-phenyl]-butyric acid (0.14 g, 0.41 mM) obtained in Example 38 and N,N-dimethylformamide-tert-dibutylacetal (0.33 g, 1.63 mM) in toluene (10 ml) was refluxed by heating for 1 hour. The reaction solution was washed with water, saturated aqueous sodium hydrogencarbonate and saturated brine, then dried, filtered, and concentrated under reduced pressure. The resulting residue was purified by silica gel column chromatography (n-hexane) and recrystallization (n-hexane) to obtain 4-[4-(6-dimethylamino-1-oxo-1,3-dihydro-isoindol-2-yl)-phenyl]-butyric acid tert-butyl ester (Compound 31) as pale yellow acicular crystals (63.6 mg, yield: 39.1%).

Melting point: 115-116° C.
MS m/z: 55 (100), 338 (M⁺, 96)
¹H-NMR (CDCl₃) δ: 1.45 (9H, s), 1.91 (2H, t, J=7.5 Hz), 2.25 (2H, t, J=7.5 Hz), 2.65 (2H, t, J=7.5 Hz), 3.03 (6H, s), 4.75 (2H, s), 6.96 (1H, dd, J=8.4, 2.4 Hz), 7.24 (1H, d, J=2.4 Hz), 7.23 (2H, d, J=8.7 Hz), 7.34 (1H, d, J=8.4 Hz), 7.77 (2H, d, J=8.7 Hz)

Example 55

A solution of 4-[4-(6-dimethylamino-1-oxo-1,3-dihydro-isoindol-2-yl)-phenyl]-butyric acid (35.5 mg, 1.03 mM)

obtained in Example 38 in THF (7 ml) was added with methyl iodide (1.2 ml), and the mixture was stirred at room temperature for 60 hours. The deposit was collected by filtration and dried to obtain {2-[4-(3-carboxy-propyl)-phenyl]-3-oxo-2,3-dihydro-1H-isoindol-5-yl}-dimethyl-ammonium iodide (Compound 32) as a colored powdery substance (34.5 mg, yield: 68.5%).

Melting point: 183-184° C.

MS m/z: 265 (88), 338 (100), 353 ($M^+$ −I, 3)

$^1$H-NMR (CD$_3$OD) δ: 1.93 (2H, quin, J=7.5 Hz), 2.32 (2H, t, J=7.5 Hz), 2.69 (2H, t, J=7.5 Hz), 3.77 (9H, s), 5.09 (2H, s), 7.32 (2H, d, J=8.4 Hz), 7.78 (2H, d, J=8.4 Hz), 7.94 (1H, d, J=8.4 Hz), 8.25 (1H, dd, J=8.4, 2.4 Hz), 8.33 (1H, d, J=2.4 Hz)

Example 56

A solution of 4-amino-2-(3,5-dimethyl-phenyl)-2,3-dihydro-isoindol-1-one (0.10 g, 0.40 mmol) and heptanal (0.23 g, 2.02 mmol) in THF (5 ml) was added with 95% sodium cyanoborohydride (80 mg, 1.21 mmol) and acetic acid (0.1 ml), the mixture was stirred at room temperature for 30 minutes, and then further added with acetic acid (0.1 ml), and the mixture was stirred at room temperature for 20 hours. The reaction solution was added with ethyl acetate for extraction. The ethyl acetate layer was washed with 1 N aqueous potassium hydroxide and saturated brine, dried over sodium sulfate, filtered, and concentrated under reduced pressure. The resulting residue was purified by silica gel column chromatography (n-hexane:ethyl acetate=6:1) and recrystallization (ethyl acetate/n-hexane) to obtain 2-(3,5-dimethyl-phenyl)-4-heptylamino-2,3-dihydro-isoindol-1-one (Compound 33) as white crystals (53.3 mg, yield: 37.7%).

Melting point: 68-69° C.

MS m/z: 265 (100), 350 ($M^+$, 43)

$^1$H-NMR (CDCl$_3$) δ: 0.92 (3H, t, J=7.2 Hz), 1.24-1.48 (8H, m), 1.62-1.73 (2H, m), 2.36 (6H, s), 3.24 (2H, t, J=7.2 Hz), 3.49 (1H, brs), 4.62 (2H, s), 6.75-6.87 (2H, m), 7.28 (1H, d, J=7.8 Hz), 7.38 (1H, t, J=7.8 Hz), 7.49 (2H, s)

Example 57

A solution of 3-dimethylaminobenzoyl chloride (0.19 g, 1.01 mmol) in THF (6 ml) was added dropwise to a solution of 4-(4-aminophenyl)butyric acid ethyl ester (0.26 g, 1.24 mmol) and triethylamine (0.31 g, 3.11 mmol) in THF (8 ml) under ice cooling. The reaction solution was stirred at room temperature for 8 hours, then added with water, and extracted with ethyl acetate. The ethyl acetate layer was washed with saturated aqueous ammonium chloride and saturated brine, then dried over sodium sulfate, filtered, and concentrated under reduced pressure. The resulting residue was purified by silica gel column chromatography (n-hexane:ethyl acetate=15:1) to obtain 4-[4-(3-dimethylamino-benzoylamino)-phenyl]-butyric acid ethyl ester as a brown oily substance (0.36 g, yield: 97.5%).

Example 58

By using 4-[4-(3-dimethylamino-benzoylamino)-phenyl]-butyric acid ethyl ester obtained in Example 57 instead of 4-[4-(5-dimethylamino-1-oxo-1,3-dihydro-isoindol-2-yl)-phenyl]-butyric acid ethyl ester used in Example 34, synthesis was performed in the same manner as that of Example 34 to obtain 4-[4-(3-dimethylamino-benzoylamino)-phenyl]-butyric acid (Compound 34) as a pale brown powdery substance.

Melting point: 127-128° C.

MS m/z: 148 (100), 326 ($M^+$, 35)

$^1$H-NMR (CDCl$_3$) δ: 1.97 (2H, t, J=7.5 Hz), 2.38 (2H, t, J=7.5 Hz), 2.67 (2H, t, J=7.5 Hz), 3.02 (6H, s), 6.88 (1H, dd, J=8.1, 2.7 Hz), 7.07 (1H, d, J=8.1 Hz), 7.19 (2H, d, J=8.7 Hz), 7.33 (1H, d, J=8.1 Hz), 7.56 (2H, d, J=8.7 Hz), 7.77 (1H, s)

Example 59

By using 2-methyl-5-nitrobenzoyl chloride instead of 3-dimethylaminobenzoyl chloride used in Example 57, synthesis was performed in the same manner as that of Example 57 to obtain 4-[4-(2-methyl-5-nitro-benzoylamino)-phenyl]-butyric acid ethyl ester as white crystals.

Example 60

By using 4-[4-(2-methyl-5-nitro-benzoylamino)-phenyl]-butyric acid ethyl ester obtained in Example 59 instead of 7-nitro-2-phenyl-2,3-dihydro-isoindol-1-one used in Example 26, synthesis was performed in the same manner as that of Example 26 to obtain 4-[4-(5-amino-2-methyl-benzoylamino)-phenyl]-butyric acid ethyl ester as a brown oily substance.

Example 61

By using 4-[4-(5-amino-2-methyl-benzoylamino)-phenyl]-butyric acid ethyl ester obtained in Example 60 instead of 5-amino-2-(4-propyl-phenyl)-isoindol-1-one used in Example 3, synthesis was performed in the same manner as that of Example 3 to obtain 4-[4-(5-dimethyl-amino-2-methyl-benzoylamino)-phenyl]-butyric acid ethyl ester (Compound 35) as a pale yellow powdery substance.

Melting point: 109-110° C.

MS m/z: 162 (100), 368 ($M^+$, 29)

$^1$H-NMR (CDCl$_3$) δ: 1.26 (3H, t, J=7.2 Hz), 1.94 (2H, t, J=7.5 Hz), 2.32 (2H, t, J=7.5 Hz), 2.38 (3H, s), 2.64 (2H, t, J=7.5 Hz), 2.94 (6H, s), 4.13 (2H, q, J=7.2 Hz), 6.75 (1H, dd, J=8.4, 2.7 Hz), 6.84 (1H, d, J=2.7 Hz), 7.11 (1H, d, J=8.4 Hz), 7.18 (2H, d, J=8.4 Hz), 7.38 (1H, s), 7.54 (2H, d, J=8.4 Hz)

Example 62

By using 4-[4-(5-dimethyl-amino-2-methyl-benzoylamino)-phenyl]-butyric acid ethyl ester obtained in Example 61 instead of 4-[4-(5-dimethylamino-1-oxo-1,3-dihydro-isoindol-2-yl)-phenyl]-butyric acid ethyl ester used in Example 34, synthesis was performed in the same manner as that of Example 34 to obtain 4-[4-(5-dimethyl-amino-2-methyl-benzoylamino)-phenyl]-butyric acid (Compound 36) as a pale brown powdery substance.

Melting point: 120-121° C.

MS m/z: 162 (100), 340 ($M^+$, 32)

$^1$H-NMR (CD$_3$OD) δ: 1.96 (2H, t, J=7.2 Hz), 2.38 (2H, t, J=7.2 Hz), 2.41 (3H, s), 2.67 (2H, t, J=7.2 Hz), 2.97 (3H, s), 7.15-7.25 (3H, m), 7.55 (2H, d, J=7.5 Hz)

Example 63

By using 2-methyl-5-nitrobenzoyl chloride instead of 3-dimethylaminobenzoyl chloride used in Example 57, synthesis was performed in the same manner as that of Example 57 to obtain 4-[4-(2-methyl-5-nitro-benzoylamino)-phenyl]-butyric acid ethyl ester (Compound 37) as white crystals.

Melting point: 108-109° C.

MS m/z: 164 (100), 370 ($M^+$, 9)

¹H-NMR (CDCl₃) δ: 1.26 (3H, t, J=7.2 Hz), 1.96 (2H, t, J=7.5 Hz), 2.33 (2H, t, J=7.5 Hz), 2.62 (3H, s), 2.66 (2H, t, J=7.5 Hz), 4.14 (2H, q, J=7.2 Hz), 7.21 (2H, d, J=9.0 Hz), 7.43-7.58 (3H, m), 8.21 (1H, dd, J=8.4, 2.4 Hz), 8.36 (1H, d, J=2.4 Hz)

Example 64

By using 4-[4-(2-methyl-5-nitro-benzoylamino)-phenyl]-butyric acid ethyl ester obtained in Example 63 instead of 4-[4-(5-dimethylamino-1-oxo-1,3-dihydro-isoindol-2-yl)-phenyl]-butyric acid ethyl ester used in Example 34, synthesis was performed in the same manner as that of Example 34 to obtain 4-[4-(2-methyl-5-nitro-benzoylamino)-phenyl]-butyric acid (Compound 38) as white crystals.

Melting point: 172-173° C.
MS m/z: 164 (100), 342 (M⁺, 3)
¹H-NMR (CD₃OD) δ: 1.92 (2H, t, J=7.5 Hz), 2.31 (2H, t, J=7.5 Hz), 2.57 (3H, s), 2.66 (2H, t, J=7.5 Hz), 7.22 (2H, d, J=8.7 Hz), 7.56 (1H, d, J=8.4 Hz), 7.60 (2H, d, J=8.7 Hz), 8.24 (1H, dd, J=8.4, 2.1 Hz), 8.32 (1H, d, J=2.1 Hz)

Example 65

By using 5-methyl-2-nitrobenzoyl chloride instead of 3-dimethylaminobenzoyl chloride used in Example 57, synthesis was performed in the same manner as that of Example 57 to obtain 4-[4-(5-methyl-2-nitro-benzoylamino)-phenyl]-butyric acid ethyl ester (Compound 39) as white crystals.

Melting point: 126-127° C.
¹H-NMR (CDCl₃) δ: 1.26 (3H, t, J=7.2 Hz), 1.95 (2H, t, J=7.5 Hz), 2.32 (2H, t, J=7.5 Hz), 2.50 (3H, s), 2.65 (2H, t, J=7.5 Hz), 4.13 (2H, q, J=7.2 Hz), 7.20 (2H, d, J=9.0 Hz), 7.31-7.45 (2H, m), 7.51 (2H, d, J=9.0 Hz), 8.06 (1H, dd, J=8.4 Hz)

Example 66

By using 4-[4-(5-methyl-2-nitro-benzoylamino)-phenyl]-butyric acid ethyl ester instead of 4-[4-(5-dimethylamino-1-oxo-1,3-dihydro-isoindol-2-yl)-phenyl]-butyric acid ethyl ester used in Example 34, synthesis was performed in the same manner as that of Example 34 to obtain 4-[4-(5-methyl-2-nitro-benzoylamino)-phenyl]-butyric acid (Compound 40) as white crystals.

Melting point: 152-153° C.
¹H-NMR (CD₃OD) δ: 1.97 (2H, t, J=7.5 Hz), 2.391 (2H, t, J=7.5 Hz), 2.50 (3H, s), 2.68 (2H, t, J=7.5 Hz), 7.21 (2H, d, J=8.7 Hz), 7.35-7.39 (2H, m), 7.52 (2H, d, J=8.7 Hz), 8.06 (1H, d, J=8.4 Hz)

Test Example 1

The reporter assay was used, in which Hela cells transfected with each of a pcDNA3 vector incorporated with the human RORα1 so that the gene can be expressed in animal cells as an expression vector, and a pGL3 promoter vector of which SV40 promoter was replaced with TK promoter as a luciferase expression reporter vector were used.

The Hela cells were placed at a density of 2×10^4 cells/0.1 mL/well on a 96-well cell culture plate (FALCON) by using 10% FBS-DMEM. On the next day, the human RORα1 expression vector, the reporter vector incorporated with 3 copies of rev-DR2 sequences and the HSV thymidine kinase promoter at a position upstream from the luciferase (Luc) gene, and a β-galactosidase (β-Gal) expression vector for control were introduced into the cells by using a transfection reagent (Fugene6, Roche). On the next day, the medium was replaced with 5% FBS-DMEM containing a test compound diluted at a prescribed concentration, after about 1 day, the cell supernatant was removed, then the cells were lysed (Passive Lysis buffer, Promega), the Luc substrate (PicaGene, Toyo Ink) was added to a part of the lysed cells, and the activity of produced Luc was measured as luminescence intensity. Further, the β-Gal activity was measured as intensity of fluorescence generated when 4-methylumbelliferyl β-D-galactoside was added as a substrate, and the activity of Luc corrected for the transfection efficiency with the β-Gal activity was used as the index for evaluation. The results are shown in Table 2. A smaller number indicates inhibitory action, and a larger number indicates promoting action. It was demonstrated that the compounds of the present invention had an inhibitory action or promoting action on the luciferase activity, and the luciferase activity was successfully regulated by using the compounds of the present invention.

TABLE 2

| | Results | | | |
|---|---|---|---|---|
| Compound | 10 μM | 1 μM | 0.1 μM | 0.01 μM |
| 2 | 3.0 | 2.8 | — | — |
| 7 | 1.1 | 1.1 | 1.1 | 1.0 |
| 10 | 0.4 | 0.3 | 0.7 | 0.9 |
| 11 | 2.6 | 2.1 | — | — |
| 14 | 2.4 | 3.1 | 2.6 | 1.9 |
| 17 | 0.0 | 0 | 0 | 0.2 |
| 18 | 0.0 | 0.0 | 0 | 0.1 |
| 23 | 0.5 | 0.6 | 0.9 | 0.8 |
| 24 | 0.4 | 0.5 | 0.7 | 0.9 |
| 28 | 0.1 | 0.2 | 0.8 | 1.1 |
| 29 | 0.0 | 0.0 | 0.2 | 0.5 |
| 31 | 0.0 | 0.1 | 0.4 | 0.8 |
| 40 | 0.8 | 0.8 | 0.9 | 0.8 |

What is claimed is:

1. A compound of formula (I) or a salt thereof:

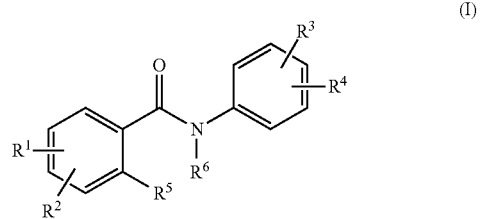

wherein $R^1$ represents a group selected from the group consisting of a halogen atom, an amino group, or a mono- or dialkyl-substituted amino group;

$R^2$ represents a hydrogen atom;

$R^3$ represents a 3-carboxy-1-propyl group wherein the carboxyl group may form an ester;

$R^4$ represents a hydrogen atom; and $R^5$ and $R^6$ bind together to become a methylene group (—CH₂—) and thereby form a 5-membered ring.

2. 4-[4-(6-Dimethylamino-1-oxo-1,3-dihydro-isoindol-2-yl)-phenyl]-butyric acid or an alkyl ester thereof, 4-[4-(6-fluoro-1-oxo-1,3-dihydro-isoindol-2-yl)-phenyl]-butyric acid or an alkyl ester thereof, or 4-[4-(6-dimethylamino-1-oxo-1,3-dihydro-isoindol-2-yl)-phenyl]-butyric acid or an alkyl ester thereof.

3. 6-Dimethylamino-2-(4-propyl-phenyl)-isoindol-1-one, 5-dimethylamino-2-(4-cyclohexyl-phenyl)-isoindol-1-one, or 7-dimethylamino-2-(4-methoxyphenyl)-2,3-dihydro-isoindol-1-one.

4. A composition for inhibiting luciferase activity, which comprises the compound of formula (I) or a salt thereof according to claim 1.

5. A composition for inhibiting luminescence for a bioluminescence system containing a luciferase and luciferin, which comprises the compound of formula (I) or a salt thereof according to claim 1.

6. A method for inhibiting luciferase activity, which comprises contacting the compound of formula (I) or a salt thereof according to claim 1 with luciferase.

7. A method for inhibiting luminescence for a bioluminescence system containing a luciferase and luciferin, which comprises combining the compound of formula (I) or a salt thereof according to claim 1 with the bioluminescence system.

\* \* \* \* \*